(12) United States Patent  (10) Patent No.: US 8,366,605 B2
Wehrheim  (45) Date of Patent: Feb. 5, 2013

(54) ENDOSCOPIC INSTRUMENT HAVING A BENDABLE SHANK

(75) Inventor: Frank Wehrheim, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 725 days.

(21) Appl. No.: 12/560,764

(22) Filed: Sep. 16, 2009

(65) Prior Publication Data

US 2010/0069719 A1    Mar. 18, 2010

(30) Foreign Application Priority Data

Sep. 17, 2008  (DE) ......................... 10 2008 047 776

(51) Int. Cl.
A61B 1/00    (2006.01)
(52) U.S. Cl. ....................................... 600/139; 600/152
(58) Field of Classification Search .................. 600/152, 600/139
See application file for complete search history.

(56) References Cited

U.S. PATENT DOCUMENTS

| 6,770,027 | B2* | 8/2004 | Banik et al. | 600/146 |
|---|---|---|---|---|
| 6,936,003 | B2* | 8/2005 | Iddan | 600/114 |
| 7,744,619 | B2* | 6/2010 | Eidenschink | 606/194 |
| 2003/0006669 | A1* | 1/2003 | Pei et al. | 310/309 |
| 2004/0068161 | A1 | 4/2004 | Couvillon | |
| 2006/0258912 | A1 | 11/2006 | Belson et al. | |
| 2007/0222344 | A1 | 9/2007 | Kornbluh et al. | |
| 2009/0048488 | A1 | 2/2009 | Uchimura | |
| 2011/0282149 | A1* | 11/2011 | Vargas et al. | 600/114 |

FOREIGN PATENT DOCUMENTS

EP  1 884 185 A1   2/2008
WO  2007057132 A1  5/2007

OTHER PUBLICATIONS

EP Search Report issued Mar. 6, 2012 in EP Application No. 09009468.1; Written Opinion.

* cited by examiner

*Primary Examiner* — Christopher Mahoney
(74) *Attorney, Agent, or Firm* — Panitch Schwarze Belisario & Nadel LLP

(57) ABSTRACT

An endoscopic instrument includes a shank which is bendable in at least one section and an endoscope head forming the distal end of the shank and in which the distal-side interfaces of the instrument are arranged. The endoscope head is bendable and is designed as one piece from an electroactive polymer. Electrodes are arranged in the endoscope head in the polymer, which may be subjected to electrical voltage.

17 Claims, 8 Drawing Sheets

ENDOSCOPIC INSTRUMENT HAVING A BENDABLE SHANK

BACKGROUND OF THE INVENTION

The invention relates to an endoscopic instrument having a shank which is bendable in at least one section and having an endoscope head which forms the distal end of the shank and in which the distal-side interfaces of the instrument are arranged.

Apart from endoscopic instruments with rigid shanks, instruments with flexible shanks are also known which may be deflected, for example via pull cables. The mechanics for deflecting or bending the shank, which are provided in these instruments, take up a certain cross-sectional area of the shank, so that the usable lumen in the inside of the shank is limited. Moreover, only limited degrees of freedom may be realized on deflection with such shanks.

Moreover, endoscopes are known which comprise electrically actuated actuators in the shank, in order to deflect the shank. Such an instrument is known, for example, from European patent application publication EP 1 884 185 A1. These instruments, however, are relatively complicated to assemble, since they require a multitude of individual parts and electrical connections in the inside.

BRIEF SUMMARY OF THE INVENTION

Having regard to this state of the art, it is the object of the invention to provide an endoscopic instrument which comprises a deflectable or bendable shank, wherein a simple manufacture of the instrument and a restriction as low as possible of the usable lumen in the inside of the instrument are provided.

This object is achieved by an endoscopic instrument having a shank, bendable in at least one section, with an endoscope head forming the distal end of the shank and holding the distal-side interfaces of the instrument. The endoscope head is bendable and is designed as one piece from an electroactive polymer. Electrodes are arranged in the endoscope head in the polymer, which may be subjected to electrical voltage The endoscopic instrument according to the invention, which may be applied for medical as well as technical purposes, comprises a shank which is bendable or flexible. This means that the shank may be bent or curved with respect to its longitudinal axis in the extended condition.

An endoscope head, as part of the shank, is formed on the distal end of the shank, in which head the distal-side interfaces of the instrument are arranged. The distal-side interfaces are the exit openings of the channels, for example access channels for tools or rinsing channels, as well as windows of illumination devices and/or optics. Moreover, these interfaces may also contain windows or objective openings of cameras and likewise. This means that the distal-side interfaces are the exit openings or end regions of all channels, instruments and observation devices and/or illumination devices, which are arranged in the inside of the instrument shank.

According to one embodiment of the invention, the endoscope head forms a bendable section of the shank. This means that the distal end region of the shank, which is formed by the endoscope head, may be angled or deflected with respect to the longitudinal axis of the shank. Thereby, preferably a maneuverability in all radial directions with respect to the longitudinal axis of the instrument is provided. This means that the endoscope head may be angled into every angle direction between 0° and 360° with respect to the longitudinal axis of the shank. According to an embodiment of the invention, the endoscope head is formed as one piece from an electroactive polymer. This means that the peripheral wall as well as, in particular, the distal-side end wall of the endoscope head are formed as one piece from this polymer. Thereby, the electroactive polymer forms the supporting structure of the shank in the region of the endoscope head. This structure gives the endoscope head the required mechanical strength. It is conceivable to provide the polymer on the outer side with an additional protective layer for the chemical preparation of the endoscope. This may be designed for example as an outer layer based on adhesion or cohesion. Preferably however, no additional outer shank is deposited into the outer side of the polymer. The manufacture and assembly of the endoscope head is significantly simplified in this manner, since the endoscope head may be cast as one piece from the electroactive polymer. It does not need to be assembled from individual parts. Moreover, no additional outer shank needs to be provided for the protection of the actuators.

The electroactive polymer simultaneously forms the actuator which effects the deflection of the endoscope head with respect to the longitudinal axis of the instrument. For this, electrodes are arranged in the endoscope head in the polymer, which are subjected to an electrical voltage. The application of a voltage effects a size change of the polymer actuator, which is used for the deformation or deflection of the endoscope head. The deflection, however, is achieved by the electrical voltage by being applied only to selected electrodes or electrode groups, and not simultaneously to all electrodes arranged distributed on the periphery. Thus, one achieves a length change of the polymer in the direction of the longitudinal axis of the shank only in a certain peripheral section, which leads to a deflection of the instrument in the desired radial direction.

The single-piece design from the electroactive polymer permits the integrated design of the endoscope head, which unifies the distal-side interfaces of the instrument and the actuator or actuators for deflecting the shank, in one component. No complicated assembly steps are required, since this component may be manufactured, for example cast, as one piece. Moreover, due to the fact that the polymer itself forms the outer wall or peripheral wall of the shank in the region of the endoscope head, one may reduce the required wall thickness, and thus the lumen available in the inside of the endoscope or shank may be increased. This means that the required construction space for receiving the actuators may be reduced by the integration of the actuators into the mechanically supporting wall of the endoscope head, and ideally no additional construction space is required.

Preferably the electrodes are cast into the polymer. The electrodes are designed such that they may assume the movements of the endoscope head when it is deflected. The casting of the electrodes into the polymer permits a simple manufacture, since one may make do without an assembly of the electrodes on the polymer. Rather, the electrodes may be arranged in the endoscope head at the desired positions in one production step with the formation of the integrated endoscope head.

Preferably, the electrodes comprise at least one electrode group consisting of at least one control electrode and of at least one reference electrode. The voltage for the size change of the polymer is applied between the reference electrode and the control electrode. The reference electrode and control electrode in the electroactive polymer are preferably spaced from one another in the axial direction, i.e., in the direction of the longitudinal axis of the instrument, so that preferably the maximal length change may be achieved in this direction by applying the electrical voltage in the polymer.

Preferably, the endoscope head comprises several electrode groups, which are arranged at different angular positions with respect to the longitudinal axis of the instrument. A deflection of the electrode head in different radial directions with respect to the longitudinal axis may be achieved by this arrangement of the electrode groups. In the minimal configuration, usefully three electrode groups uniformly distributed over the periphery of the longitudinal axis are provided. Thereby, one may achieve a deflection in different angular directions depending on the electrode groups which are subjected to voltage. One may achieve a finer grading of the angles or radial directions, in which a deflection is possible, by increasing the number of electrode groups which are arranged distributed over the periphery. In the ideal case, a deflection in any radial direction with respect to the longitudinal axis of the instrument may be achieved by also subjecting several electrode groups to voltage simultaneously, as the case may be. Thus, one may realize a maneuverability of the instrument as large as possible in any direction.

According to a further preferred embodiment, the endoscope head may comprise several electrode groups, which are arranged at different axial positions with respect to the longitudinal axis of the instrument. The electrode groups thereby are preferably designed such that they may be subjected to voltage independently of one another, so that a deflection or bending of the shank may be realized at different axial positions. Different angles of curvature may be achieved by this with the deflection of the electrode head, and also different deflection directions over the axial length of the endoscope head, so that a very large maneuverability of the endoscope head is possible in different directions. In the extreme case, the electrode head may be guided or deflected in a three-dimensional serpentine movement.

The individual electrode groups may, in each case, comprise a multitude of individual electrodes, which, as the case may be, may be simultaneously subjected to voltage. Thus, individual actuators, which in each case consist of two electrodes, may be stacked in an electrode group, so that the electrode group forms an actuator group. The individual electrodes are spaced only very slightly to one another, so that the size changes between two electrodes are very small. One may realize greater shape changes or size changes in the polymer by the stacking of such actuators in one direction, and a suitable arrangement of a multitude of electrodes one after the other.

Preferably, at least one electrode group is provided, which comprises several control electrodes which are distanced to one another in the axial direction with respect to the longitudinal axis of the instrument, and which may be subjected to voltage preferably independently of one another. The maneuverability of the instrument may be increased by independently subjecting the individual electrodes to voltage, i.e., the deformation in individual angle regions and also in the axial direction may be set in a very flexible manner, so that a large movement ability of the shank is achieved. As previously described however, one may also subject several control electrodes simultaneously to voltage, and for example group them together in a fixed manner into electrode groups which are electrically connected to one another, in order to create larger shape change regions.

The electrode groups preferably comprise a multitude of control electrodes and a multitude of reference electrodes, which are arranged alternately to one another in the axial direction. This means that a control electrode always follows a reference electrode, which effect the size change or shape change of the polymer due to a prevailing voltage. The polymer thereby preferably forms a dielectric between the electrodes. Such electrode groups, which together with the polymer, in which they are embedded, form an actuator group, are preferably arranged distributed over the periphery of the shank such that a deflection of the shank at different angular directions with respect to the longitudinal axis is possible, depending on which electrode groups are subjected to voltage.

The control electrodes and/or reference electrodes may thereby be designed such that they may be individually subjected to voltage. They may however also be grouped together into groups and electrically connected to one another. For this, preferably the multitude of control electrodes and the multitude of reference electrodes are in each case designed as a comb structure and the two comb structures mesh into one another with their teeth. Thus, a reference electrode always comes to lie between two control electrodes. The individual electrodes of each comb structure are thereby conductively connected to one another preferably at one side, i.e. at one end. The side forms the closed side of the comb. Then, the respective other electrodes mesh from the opposite side into the free spaces between the electrodes.

According to a further preferred embodiment, the reference electrode may be designed in a spiral or helical manner, and control electrodes may be arranged between the individual thread flights of the reference electrodes. The control electrodes may thereby also be designed in a helical or spiral manner. Alternatively, it is also possible to arrange individual segment-like control electrodes between the thread flights of the reference electrode, and to design the control electrodes such that they may be subjected to voltage individually or in individual groups. In this manner, it is very simply possible to form several electrode groups or actuator groups, with a common, continuous reference electrode, said groups able to be actuated or activated individually by applying an electrical voltage. In this manner, one may accommodate a multitude of electrodes in the wall of the endoscope head in a relatively space-saving manner, and these may be subjected to voltage individually or in groups, in order to be able to realize a large maneuverability of the endoscope head in different directions.

Thus, a multitude of electrode groups may comprise a common reference electrode, in particular in a helical fashion. The required electrical connections which must be arranged in the polymer may be simplified in this manner, since one does not have to electrically connect a multitude of reference electrodes to one another, but instead one may use a continuous, helical reference electrode for several electrode groups. Such a helical conductor structure may be designed in a relatively simple manner and embedded into the electroactive polymer.

The previously described design of the electrode arrangements or actuator arrangements is not limited to the described endoscope head. Rather, further bendable or deflectable sections of an electroactive polymer with electrodes arranged therein may be formed in the shank also on the proximal side of the endoscope head. Preferably, the shank over its whole length comprises sections bendable in such a manner that a very mobile shank is formed, which may also move through winding or serpentine body channels. The supporting wall or supporting structure of the shank is also formed by the electroactive polymer with these bendable sections, i.e., the electroactive polymer extends preferably essentially over the complete wall thickness of the shank. As the case may be, a coating may be arranged on the outer periphery in the manner described above with regard to the endoscope head. The arrangement of the electrodes and their function, with such bendable, proximal-side shank sections, also corresponds to the designs described previously with regard to the endoscope head.

Usefully, the electrodes are provided with control leads which extend to the proximal end of the shank. There, they may then be connected to a control device, which activates the individual actuators. The control leads are preferably designed as metallic conductors, which are embedded into the wall material of the shank, which preferably comprises a plastic, particularly preferably likewise of an electroactive polymer. They may, however, also be attached on the inner side or outer side of the shank wall. These control leads are likewise bendable in the bendable or movable sections of the shank. They may be designed in a rigid manner in likewise rigid sections. The embedding in a plastic has the advantage that the electrical insulation is simultaneously ensured by this. Moreover, the assembly is simplified, since the electrical conductors or control leads may be embedded into the shank on casting the plastic into the mold/shape of this.

According to a further preferred embodiment, the endoscope head comprises at least one force sensor arranged at the distal end. Thereby, the force sensor is preferably oriented such that it may detect at least one force component acting in the direction of the longitudinal axis of the shank. Preferably, a plurality of force sensors is arranged at the distal end, in particular on the end-face of the distal end. The force sensors are thereby advantageously distributed over the periphery close to the outer periphery. Particularly preferably, the force sensors are oriented with their main acting direction inclined, e.g., in a direction of 45° to the longitudinal axis of the instrument or to the advance direction of the instrument. Thus, they may detect force components which act in the peripheral direction onto the shank, and force components which act in the longitudinal direction of the shank. The force sensors serve for being able to rapidly detect an abutting of the distal end of the endoscope onto tissue parts, in order to prevent damage to the tissue on advancing. Thus, the force sensors, as described hereinafter, may cooperate with a control device which controls the deflecting or the bending of the endoscope head.

One may precisely detect at which peripheral angle the endoscope abuts due to the arrangement of a multitude of force sensors distributed over the periphery of the distal-side end-face, so that the endoscope may be deflected in the opposite direction and advanced further.

The force sensor or sensors may, for example, be designed as capacitive force sensors. Usefully, the force sensors are embedded or cast directly into the electroactive polymer. In the ideal case, only electrodes are necessary for this. The capacitance change between the electrodes is effected by elastic compression of the polymer between the electrodes of the sensor.

Preferably, a control device is provided, which is connected to the force sensor or force sensors in a manner such that it receives signals from the force sensors, which are representative of the force detected in each case. The connection is effected preferably in an electrical manner, i.e., electrical signals are produced by the force sensors, which are transmitted to the control device. The control device evaluates the detected force signals.

Moreover, the control device is designed in a manner such that it controls the actuators for deflecting the shank. This means that the control device causes the actuators to deflect the shank in a certain manner Thereby, the control device is designed such that the actuators are controlled by the control device while taking into account the force detected by the force sensor. This permits an automatic or partly automatic control of the deflection of the endoscope in dependence on the forces acting on the distal end-side. Thus, in the case that a force which acts on the distal end-side of the endoscope is detected by the force sensor, the control device may deflect the shank or the endoscope head by control of the actuators, in order to prevent a further advance in the direction of the acting force. Damage to vessels on advance of the instrument may be avoided in this manner, since an automatic evasion of obstacles is made possible by the control device. A force acts on the force sensor when an obstacle opposes the endoscope on its advance. One may dodge this obstacle by a suitable deflection of the shank. It is simultaneously possible for the respective obstacle to be signaled from the control device to the operating person. This may be effected, for example, in an optical, acoustic or also haptic manner.

Preferably, several force sensors are arranged on the end-side edge region at the distal end of the shank, preferably in a manner such that a force acting on the distal end may be determined depending on direction. The arrangement at the distal end region, i.e., on the outer periphery of the distal end-face, has the advantage that indeed obstacles which are only contacted by the edge region of the distal end may be detected via the force sensors. In the case that several force sensors are arranged distributed over the periphery of the distal end-face, one may also detect the peripheral region at which the obstacle opposes the instrument. The control device may react accordingly and control the actuators such that the shank is deflected in an opposite direction, in order to evade the obstacle. Thus, one may determine from which direction the force comes from, i.e., in which direction the obstacle obstructs the advance, by the several force sensors. Particularly preferably, the force sensors are arranged at the edge region of the distal end, such that they not only detect a force in the axial direction with respect to the longitudinal axis of the extended instrument shank, but also force components which act on the end in the radial direction. Thus, the force sensors may be arranged at an angle to the end-face and to the longitudinal axis, for example 45°, so that their main direction of acting is inclined to the longitudinal axis and to the end-face. In this manner, one may even better detect obstacles which obstruct the advance of the instrument at the edge region of the distal end-side.

It is further preferable for the control device to be connected to operating elements, via which the deflection of the shank may be set. This permits a semi-manual movement control. A user of the instrument may preselect the advance direction and thus the required deflection of the endoscope head via the operating elements. This may be effected for example on the basis of a picture produced by the endoscope optics. The control device then controls the actuators, such that the shank of the instrument, i.e., in particular its distal end or the endoscope head, is deflected or angled by the actuators in a suitable manner. Simultaneously, the control device however is also connected to the force sensors, and may automatically initiate a deflection when the force sensors detect a resistance. Thereby, the control device may be designed such that the automatic deflection is superimposed on the manual selection of deflection in an overriding manner, so that a circumnavigation of obstacles or a dodging in any case is effected automatically, independently of which deflection an operating person has manually selected.

Alternatively, it is however also possible to design the control device in a manner such that the actuators are automatically controlled in dependence on the force detected by the at least one force sensor. The control device may achieve a fully automatic deflection on advance in this manner. Thus, with the advance, the instrument may automatically follow a given channel, for example of a body opening, without the operating person having to take care with regard to the correct deflection of the instrument shank. It is to be understood that the control device may also be designed in a manner such that it selectively permits both modes, the described fully automatic mode or the previously described semi-manual mode.

Particularly preferably, the control device is designed in a manner such that on detecting a pressure force above a predefined limit value, at a force sensor, the shank is deflected in a direction opposite to the detected force by control of the actuators. The fact that the deflection is only effected above a certain limit value makes sense, in that slight resistances which result due to the friction on advance of the instrument may be ignored, and only those forces are taken into account by the control device, which indeed are due to an obstacle. As described above, it is preferable to arrange several force sensors at the distal end-side of the shank, which detect occurring forces in a direction-dependent manner. Then, on the basis of the direction-dependent force detection, it is possible for the control device to control the actuators, such that the shank is deflected in an opposite direction to the occurring force. This means, for example, that if a force sensor detects an obstacle at the edge of the end-side of the instrument in a position of 0°, the shank is then deflected by actuation of the actuators by the control device, preferably in the direction of 180°. An obstacle is circumnavigated in a secure manner by this.

Further preferably, the control device is designed in a manner such that on detecting a pressure force above a predefined limit value at several force sensors, the axial advance of the shank is stopped and/or a warning signal is issued. The detection at several force sensors may be deduced as a force which acts on the end-side on the instrument end-side in the axial direction. In this case the instrument hits an obstacle in a blunt manner. An automatic deflection may no longer be effected in the case of such a blunt collision, i.e., in a dead-end. In this case, the control device is then to output a warning signal to the user, so that he may stop the advance of the instrument. In the case of an automatic advance, the advance in such a case may also be automatically stopped. The warning signal may, for example, also be optical, haptic or acoustic.

According to a further preferred embodiment, several actuators which are actuated independently of one another by the control device are arranged distributed over the axial length of the shank. This design permits a maneuverability of the shank over a greater axial length. Thereby, due to the independent activation ability of the actuators, it is possible to deflect the shank in different directions in different axial regions. Thus, the shank may also be moved in a serpentine manner. It is thus possible to also follow channels which are curved several times with the shank.

In particular, it is thereby preferable for the control device to be designed such that on advance of the shank, it controls the proximally situated actuators, such that the shank tracks the deflection caused by the distally situated actuators. This means that with the advance, the proximally situated actuators are actuated such that the curvature of the distal actuators proportionally transmits the advance movement of the shank onto the actuators in the proximal direction. Thus on advance, the shank may follow a curved channel course. In particular, it becomes possible to also follow a multiple curved channel course, also in serpentine lines. In the reverse direction, on withdrawing the instrument from the channel, the control means controls the actuators situated further distally, such that they follow the curvature. Such a control is preferably effected automatically.

For this, an automatic advance device and/or a detection device for detecting the advance are present, which cooperate with the control device. This means that in the case of a manual advance, the advance path is detected and led to the control device as an input variable, so that the control device, with the axial movement, may control the actuators such that the instrument shank follows a curved channel course. Alternatively, the complete advance may be controlled in an automatic manner, i.e., the control device also effects the advance via a drive. Thereby however, input means or operating elements may be provided, via which the user may select the desired advance. This means that here, the advance may then not be directly caused mechanically by the user, but indirectly via an intermediate control device. This design has the advantage that the control device, as described above, may automatically stop the advance in the case of a blunt collision at the distal shank end.

The force sensors are preferably embedded into a plastic material, from which the distal end of the shank is manufactured. Thus, one may integrate the force sensors into the distal end, in particular into the endoscope head. On the one hand the manufacture is simplified by this. On the other hand the spatial requirement of the sensors is kept very small, so that the useable lumen within the shank is not significantly compromised, and preferably the complete distal end-side of the shank is available for the distal interfaces, i.e., exit openings of the channels in the shank and optical elements or illuminating devices. The force sensors are preferably cast into the plastic material. Thereby, the plastic material itself may form a part of the force sensor. For example, electrodes may be cast into the plastic material distanced to one another. The force effect deforms the plastic material between the electrodes, by which the electrical resistance or the capacitance between the electrodes changes, which may be detected. One may deduce the acting force with the knowledge of the mechanical characteristics, in particular the modulus of elasticity. In this manner, the force sensors may be designed in a very simple manner in the plastic material of the shank.

In a simple manner, the effected deflection or angling of the endoscope shank may be detected in a manner such that the electrical resistance changes by the deformation of the electroactive polymer between two electrodes, which may be detected directly between the electrodes. This means that no additional sensors are to be arranged in the shank wall or the wall of the endoscope head, but rather, only the resistance between the electrodes used for actuating the actuators needs to be detected.

The endoscopic instrument according to an embodiment of the invention usefully comprises an electronic control device, which is connected to the electrodes and controls the deformation or deflection of the shank. This means that the control device subjects the required electrodes to a voltage, in order to ensure a desired movement direction or deflection direction of the shank or endoscope head. The deflection direction in semi-manual operation may thereby be additionally set by the user of the instrument via suitable operating elements.

The invention permits a special method for controlling an endoscopic instrument, which is designed in the previously described manner. According to this method, as already described above by the device, on advance of the instrument, the forces acting on the distal end of the shank are detected, and a deflection of the moving shank is initiated depending on the detected forces. In this manner, one may recognize obstacles by the force recognition, and these may be circumnavigated by a suitable deflection of the shank. The above description is referred to with regard to this.

As already described above, it is particularly preferable for the deflection of the shank to be effected in each case in a direction which is opposite to the detected force. In this manner, one dodges obstacles which are situated only in the edge region or part regions, of the distal end-face of the shank.

The advance of the instrument is preferably stopped and/or a warning signal is issued in the case that a force acting on the distal end in the axial direction is detected, so that the user of the instrument may stop the advance.

The above description of the device is referred to with regard to the more detailed design of the method, from which the respective features of the method also result.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
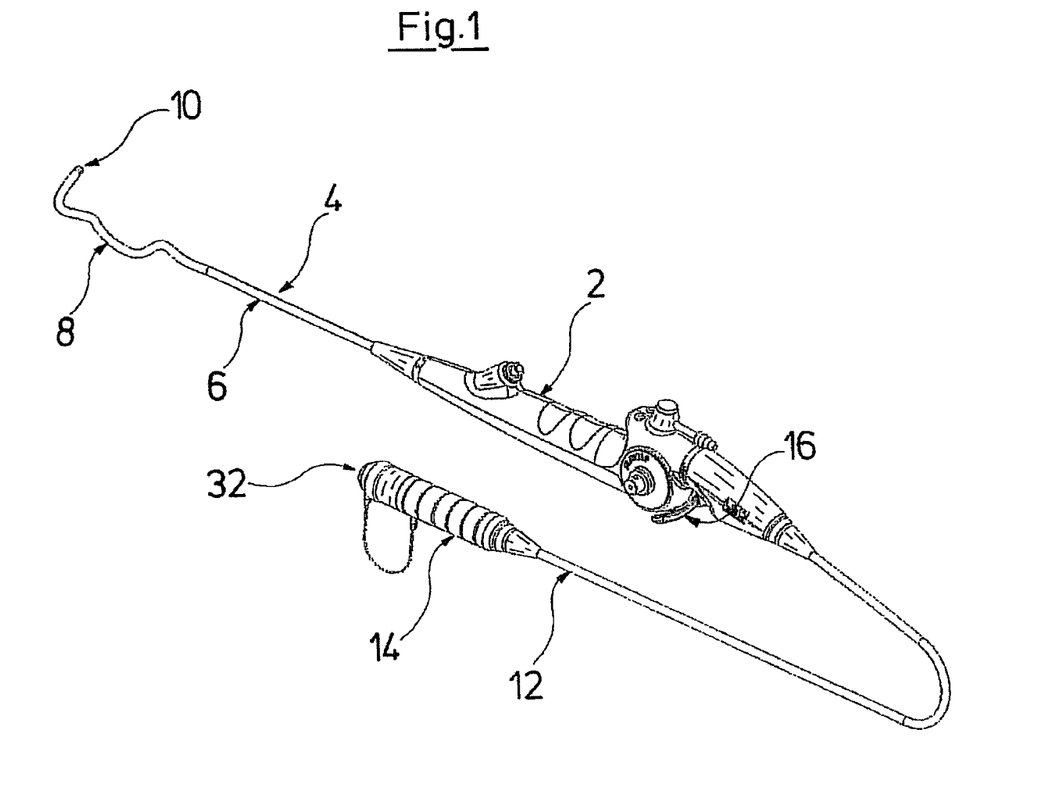
FIG. 1 is a schematic entire perspective view of a medical instrument according to one embodiment of the invention.

As FIG. 1 shows, the instrument described by example comprises a hand grip 2 arranged at the proximal end, from which a shank 4 extends distally. The shank 4 comprises a first proximal shank section 6, which is designed in a flexible manner. An actively movable endoscope head 8, whose distal end forms the distal endoscope tip 10, connects to the distal end of the shank section 6. On the proximal side, a connection cable 12 extends from the hand grip 2 and ends in a connection plug 14, with which the instrument may be connected to a control apparatus and, as the case may be, to a light source. The hand grip comprises operating elements 16, via which the deflection of the endoscope tip at the endoscope head 8 may be set.

As may be recognized in FIG. 1, the endoscope head 8 may be bent or deflected in a very flexible manner. For this, actuators which effect the deflection, are arranged in the inside of the endoscope head 8, as described hereinafter. The endoscope head 8 permits a serpentine endoscope movement which is explained in more detail by FIG. 2.

Figure 2:
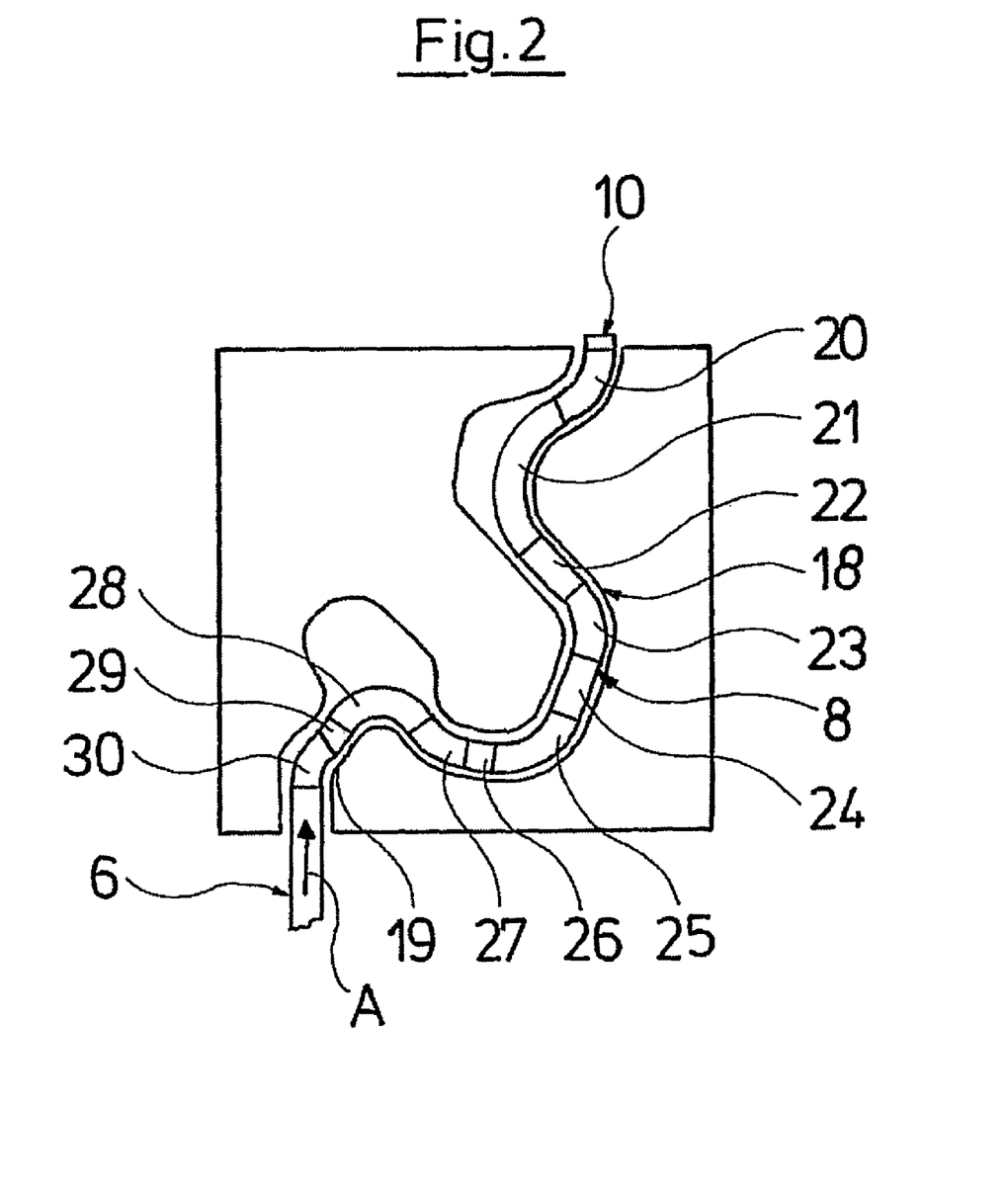
FIG. 2 is a schematic view of the angled endoscope head according to an embodiment of the invention, shown in a simplified meandering body opening.
Figure 10:
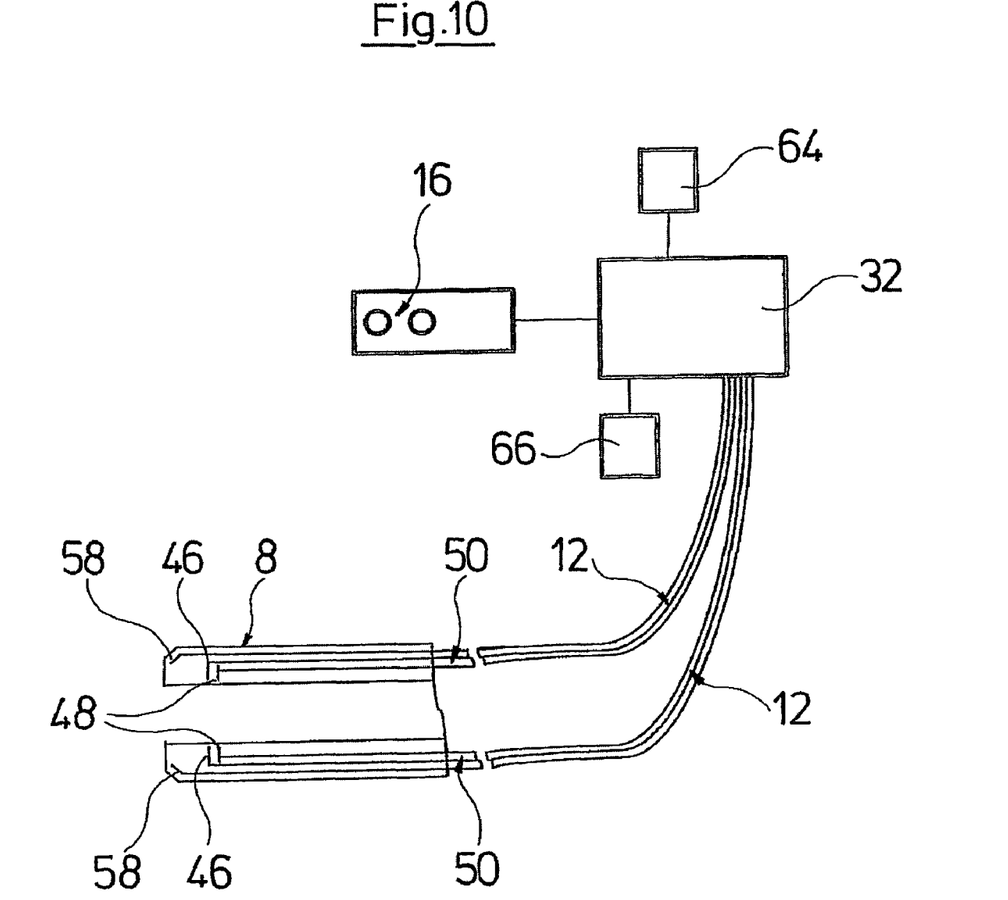
FIG. 10 is a schematic diagram of the control device for an instrument according to an embodiment of the invention.

FIG. 2 shows the endoscope head 8 in a weaving channel 18, for example a meandering body opening. For introduction, the distal end of the endoscope head 8, i.e., the endoscope tip 10 is inserted into the channel 18 in the direction of the arrow A. With the first bending, a first section 20 which connects to the endoscope tip 10 on the proximal side, is angled or curved such that the first bending 19 may be circled. With a further advance in the direction of the arrow A, the section 20 is in each case deflected or bent accordingly, such that the following curves may be circumnavigated. The sections 21-30 of the endoscope head 8 which connect proximally to the section 20, may likewise be angled, wherein with a further advance, the sections 21-30 are always bent such that they follow the movement of the first section 20, so that the endoscope head 8 may move through the channel 18 in a serpentine movement. Thereby, the deflection of the sections 20 to 30 is effected in an active manner by actuators arranged in the sections. This has the advantage that the friction on the walls of the channel 18 is reduced, since significantly smaller pressure forces occur there. Thus, as a whole, an easier advance of the instrument is possible, by which the danger of injury is reduced. The deflection of the sections 21 to 30 is preferably initiated by a control device 32 (see FIG. 10). The control device controls the deflection of the sections 21 to 30 in dependence on the advance in direction A, so that these regions track the movements of the first section 20, and as a shown, the targeted serpentine movement results.

Figure 3:
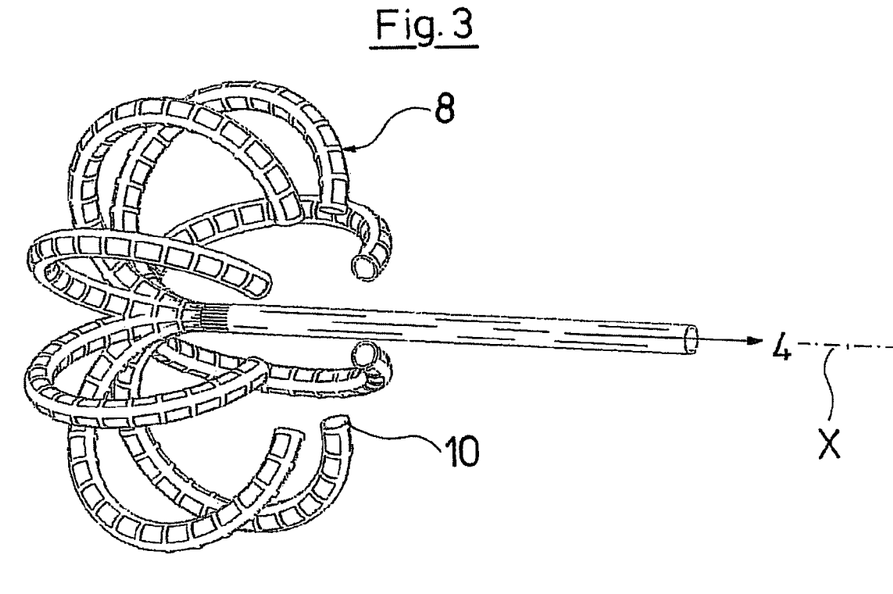
FIG. 3 is a schematic perspective view, showing the degrees of freedom of the movement of the endoscope head according to FIGS. 1 and 2.

FIG. 3 schematically shows how the endoscope head 8 may bend or deflect essentially in any radial direction with respect to the longitudinal axis X. Thereby, a bending about in each case 270° is possible, so that the endoscope tip 10 faces the longitudinal axis X of the shank 4 in the radial direction. Thus, FIG. 3 shows the maximal possible deflection and the possible deflection directions of the endoscope head 8.

The deflection of the endoscope head 8 is rendered possible by actuators arranged in the endoscope head 8. This is explained in more detail by the FIGS. 4 to 9. The endoscope head 8 is designed as an integrated component, which unifies several functions. The peripheral wall 34, as well as the end-side wall 36 on the endoscope tip 10, is manufactured of one piece of a polymer material. With this polymer material, it is the case of an electroactive polymer, i.e., a polymer which changes its shape or extension in dependence on an applied electrical voltage. The distal-side interfaces of the instrument are integrated into the end-side wall 36. In the shown example, it is thereby the case of a probe channel 38, optics 40 as well as fiber-optics 42 and 44. All these channels and elements end in the endoscope tip 10 and have their distal-side interfaces there. In a corresponding manner, picture sensors, LED light sources and likewise may be integrated as distal-side interfaces into the end-side wall 36. The end-side wall 36 and the peripheral wall 34 form the mechanically supporting structure of the endoscope head 8. This means that the peripheral wall 34 in this region forms the tube of the shank, which also simultaneously delimits the shank to the outside.

Electroactive polymers suitable for use in embodiments of the present invention are described, for example, in U.S. Patent Application Publication No. US 2007/0222344 A1. Such polymers generally include elastomers, rubbers and rubber-like materials, such as silicone elastomers, acrylic elastomers, fluoroelastomers, polyurethanes, and the like. An example of a suitable electroactive polymer for use in embodiments of the present invention is ELASTOSIL® P7670 A/B, a flowable, addition-curing two-part silicone rubber with short potlife at room temperature (RTV silicone), which is commercially available from Wacker Chemie GmbH, Munich, Germany.

Figure 4:
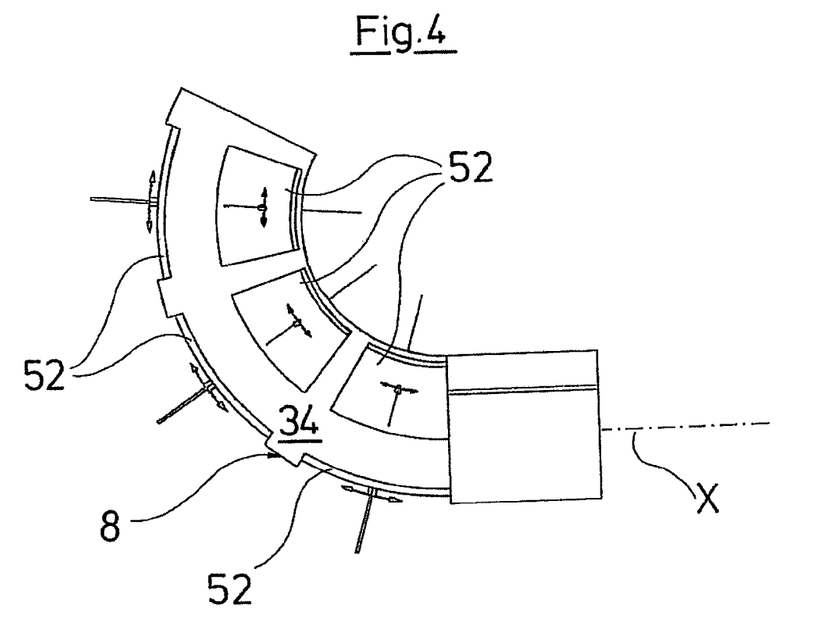
FIG. 4 is a schematic, partial side view of the arrangement of the actuators in the endoscope head according to FIGS. 1 to 3.
Figure 5:
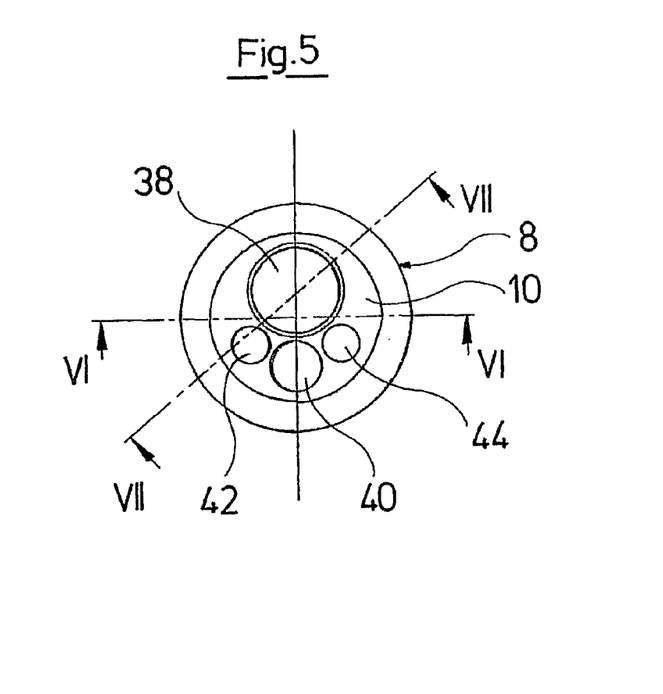
FIG. 5 is a simplified plan view of the distal end of the endoscope head.
Figure 6:
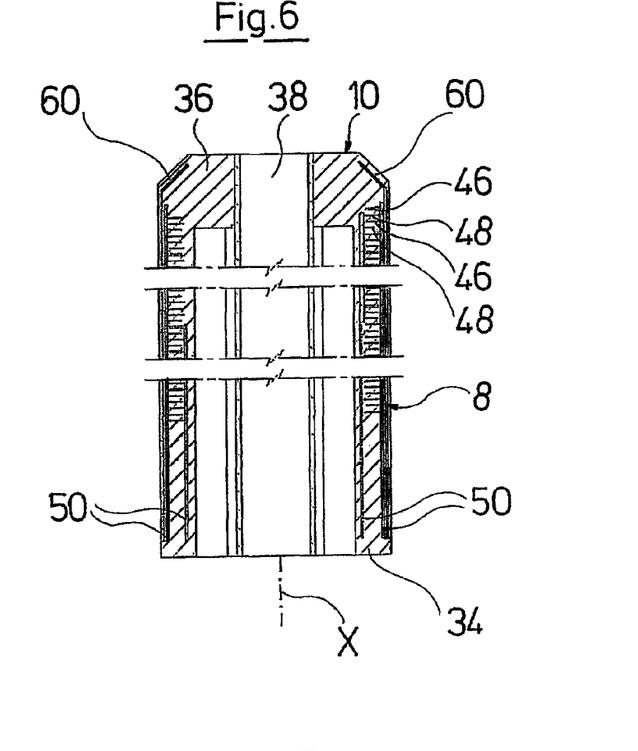
FIG. 6 is a truncated, sectioned view along the line VI-VI in FIG. 5.
Figure 7:
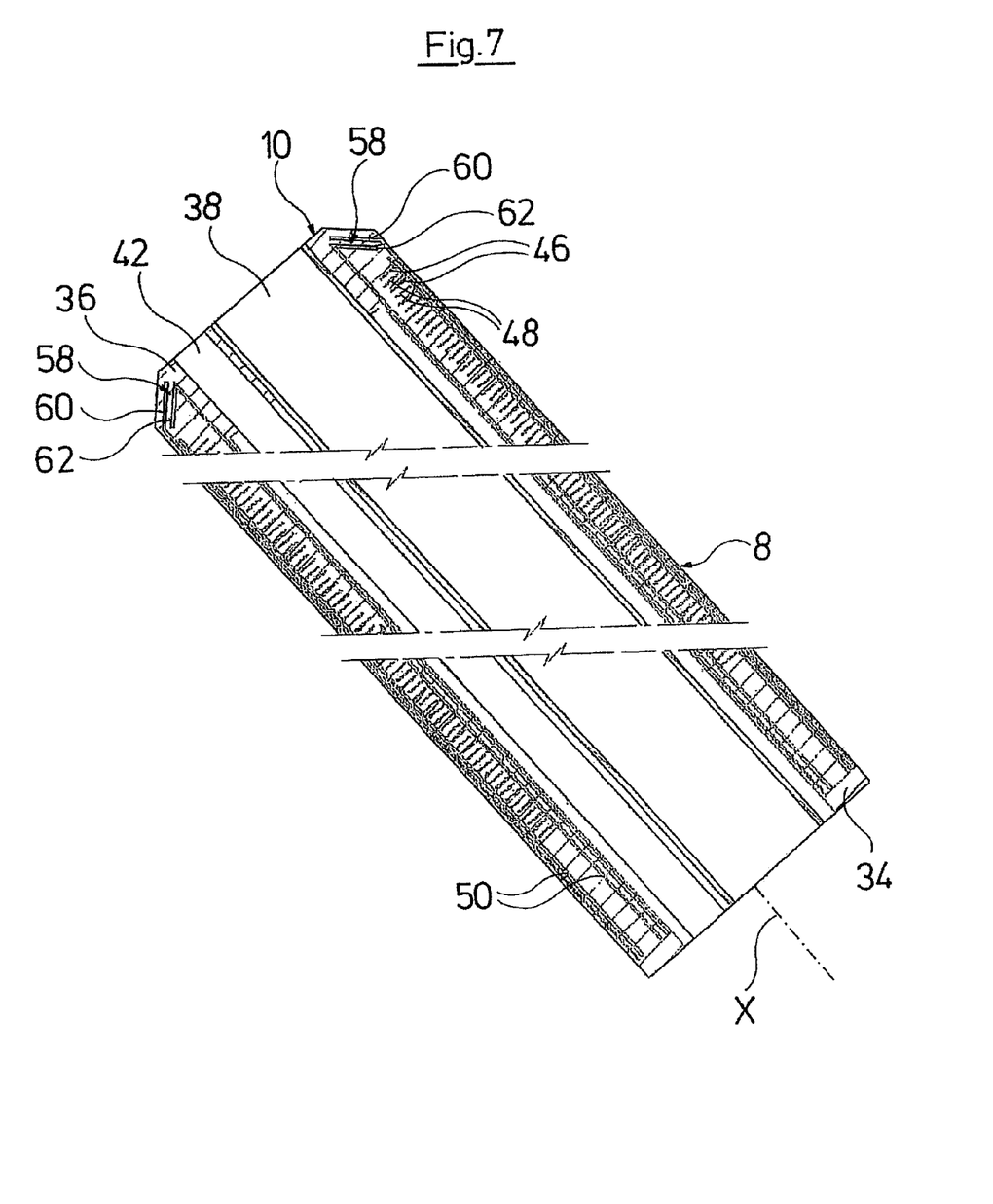
FIG. 7 is a truncated, sectioned view along line VII-VII in FIG. 5.

Electrodes 46 and 48 are embedded into the electroactive polymer. The electrodes 46 form control electrodes, while the electrodes 48 represent reference electrodes. A voltage is applied between the electrodes 46 and 48, which are arranged in the polymer 34 spaced from one another in an alternating manner, by which the extension of the polymer between the electrodes 46 and 48 changes. Length changes in the direction of the longitudinal axis X may be caused by this. Since the electrodes 46 and 48 are arranged in electrode groups, which are arranged at different locations of the periphery in the peripheral wall 34, these length changes may be selectively caused by suitable electrical voltages at the electrodes in individual peripheral regions, by which a deflection or bending out in the previously described manner may be achieved. The electrodes 46 and 48 are connected to the control device 32 via control leads 50. The control leads 50 are likewise embedded into the polymer of the wall 34 and extend in the proximal direction up to into the hand grip 2, from where they are then connected further to the control device 32 in an electrically conductive manner.

Due to the fact that the electrodes 46 and 48 are arranged directly in the peripheral wall 34, the actuators which are formed from the electrodes 46 and 48 as well as the polymer situated between the electrodes, i.e., the material of the wall 34, may be arranged in the instrument in a very space-saving manner. No additional constructional space for the actuators is required, and these may be integrated into the wall 34 or the wall itself acts as an actuator. The free lumen in the inside for channels, fiber-optics and likewise may be kept very large by this. Moreover, the construction of the instrument is very simple, since the endoscope head is designed as one piece. The endoscope tip 10 may be cast together with the peripheral wall 34 from the electroactive polymer, wherein simultaneously the electrodes 46 and 48 required for the actuators, with their control leads 50, are cast into the polymer. This means that an additional assembly for the actuators and the endoscope tip 10 is done away with.

The achievable length change between the individual electrodes 46 and 48 is also very small, since the distance between the individual electrodes 46 and 48 is very small. Several electrodes are grouped together into electrode groups for this reason. Thereby, the electrodes of an electrode group are then preferably commonly subjected to voltage, so that the individual length changes between the individual electrodes in the polymer, as a whole, add up into a larger length change. These electrode groups form actuator fields 52, which are schematically shown in FIG. 4. The electrodes are not shown in FIG. 4, but merely the regions (actuator fields 52) in which the electrodes are embedded into the peripheral wall 34. Thereby, the electrodes are cast preferably into the peripheral wall, as previously described, so that a peripheral wall arises, which is manufactured as one piece of polymer material.

The actuator fields 52 on the one hand are arranged such that several actuator fields 52 are distributed in the peripheral direction of the wall 34. This means that in this direction, the actuator fields 52 are situated at different peripheral positions, preferably distributed in a uniform manner. By this, one may achieve a deflection in a certain direction, as schematically shown in FIG. 3. The shank is deflected in the corresponding direction, depending on which of the actuator fields 52 in a cross-sectional plane is subjected to voltage. In the example shown in FIG. 4, three actuator fields 52 are distributed over the periphery. If only these three actuator fields 52 were to be selectively subjected to voltage, a deflection would only be possible in three radial directions. However, it is also possible to subject two of the actuator fields 52 simultaneously to voltage, so that a deflection is also possible in an angular direction, which is situated between two actuator fields 52. Moreover, it is also possible to vary the degree of the shape change between the electrodes and thus the deflection, by the variation of the electrical voltages, to which the electrodes of the individual actuator fields 52 are subjected. If now two actuator fields 52 in the same cross-sectional plane are subjected to different voltages, then a deflection in any infinite direction, as is shown in FIG. 3, may be achieved by a suitable choice of the voltages.

Moreover, the actuator fields 52 may also be arranged lying one after the other in the axial direction. By this, the sections 20 to 30 are created in the axial direction, which may be differently deflected, by which the serpentine flexibility of the instrument is realized, as explained by FIG. 2.

Figure 8:
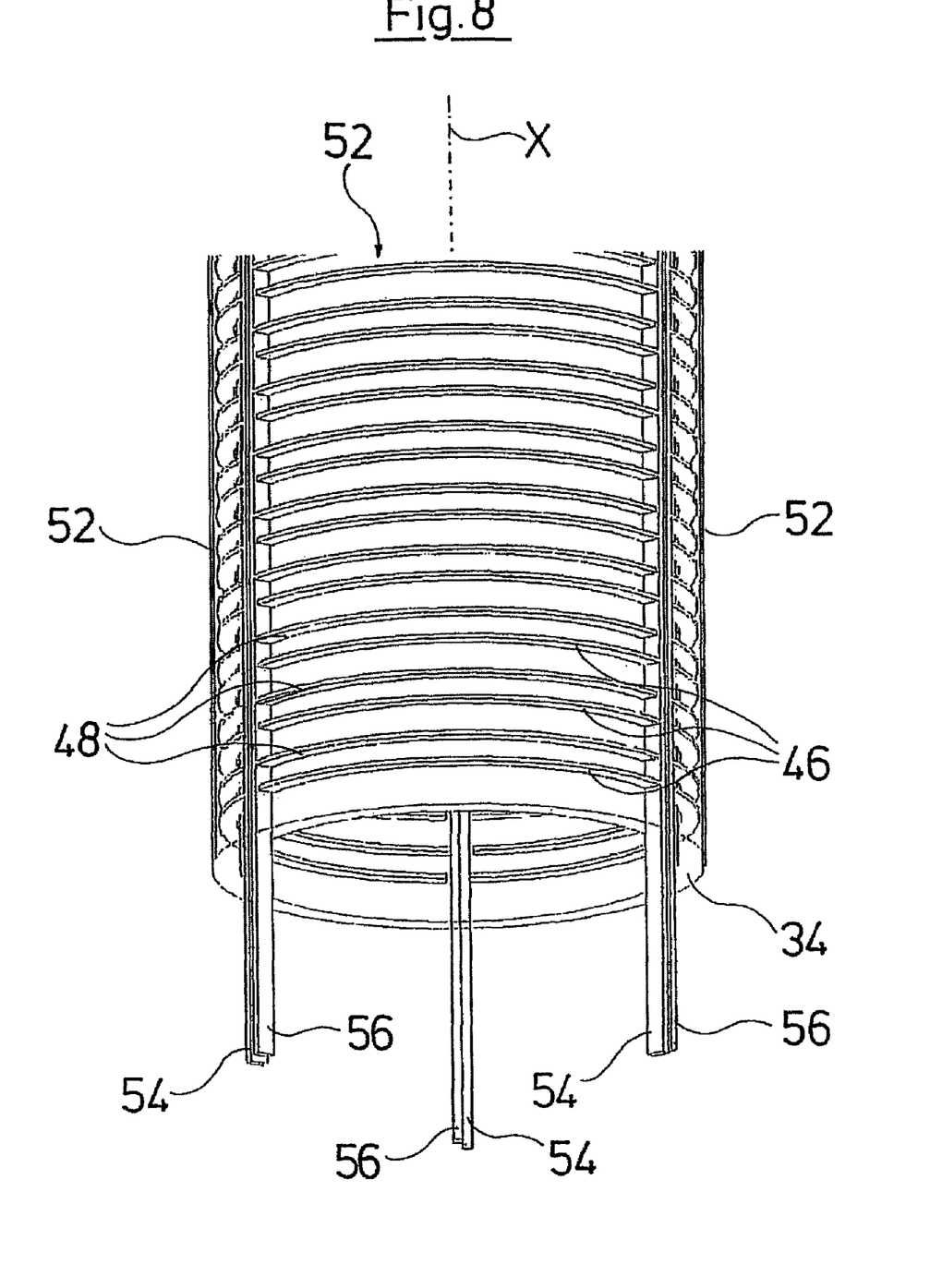
FIG. 8 is a schematic, perspective view of a first possible electrode arrangement for an actuator.

A first example for a possible arrangement of the electrodes in the actuator fields 52 is shown in FIG. 8. FIG. 8 in a circumferential plane shows three actuator fields 52, which are formed by alternately arranged electrodes 46 and 48. With the embodiment example according to FIG. 8, a comb-like electrode structure is selected. This means that the electrodes 46 proceeding from the axial conductors 54, extend in the peripheral direction in each case essentially over a third of a circle. Accordingly, proceeding from the axial conductors 56, the electrodes 48 extend in each case likewise in the peripheral direction essentially over a third of a circle. Thereby, the electrodes 46 and 48 proceeding from the axial conductors 54 and 56, extend in opposite directions, so that the electrodes 46 engage into the free spaces between the electrodes 48 or, vice versa, the electrodes 48 engage into the free spaces between the electrodes 46. Since all electrodes 46 of an actuator field 52 are connected to the associated axial conductor 54, these electrodes 46 are all together subjected to voltage with respect to the electrodes 48. The electrodes 48 of an actuator field 52 are in each case commonly connected to an axial conductor 56. The axial conductors 54 and 56 extend in the axial direction to the proximal end of the shank as control leads 50.

Figure 9:
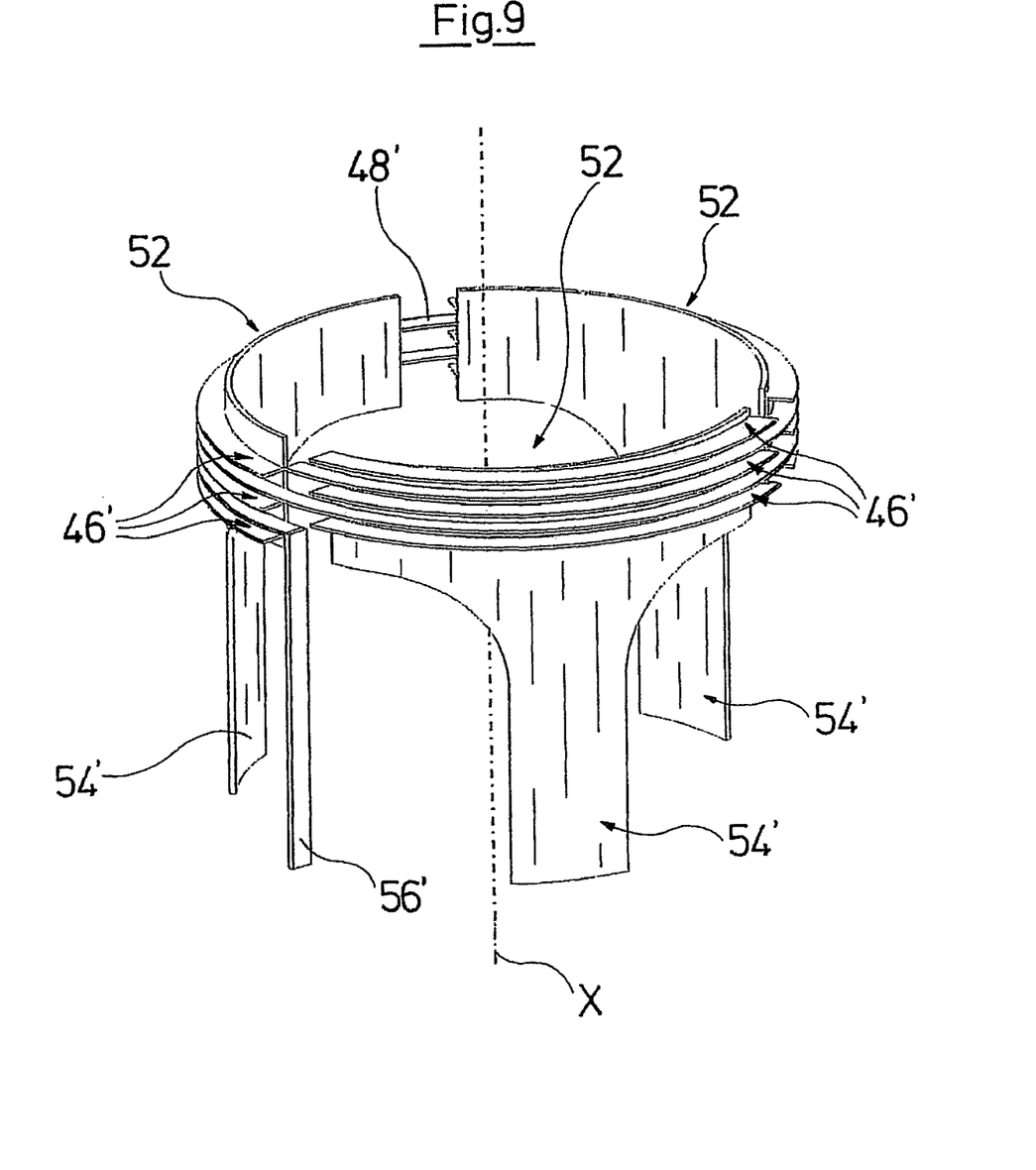
FIG. 9 is a schematic, perspective view of a second possible electrode arrangement for the actuator.

FIG. 9 shows a second possible electrode arrangement. With the arrangement according to FIG. 9, the reference electrode 48' is designed as a continuous spiral or helical reference electrode 48'. At one end, this electrode 48' is connected to an axial conductor 56' which forms a control lead 50 in the proximal direction. Also with this embodiment according to FIG. 9, three actuator fields 52 arranged distributed in the peripheral direction are also provided, which extend essentially in each case over third of a circle. The control electrodes 46' are in each case shaped in a segment-like manner and likewise extend essentially over a third of a circle. Thereby, numerous arch-shaped control electrodes 46' are arranged spaced from one another in each actuator field 52, such that they engage into the free spaces between the spiral flights of the continuous reference electrode 48'. The arch-shaped control electrodes 46' proceeding from the axial conductors 54', extend outwards in the radial direction in a web-like manner. Thus, three groups of control electrodes 46' are created, which in each case may be subjected to voltage with respect to a reference electrode 48', via one of the axial conductors 54'. In this manner, one creates three actuator fields 52 which may be activated independently of one another. The axial conductors 54' extend further in the proximal direction as control leads 50. With the embodiment according to FIG. 9, it is to be understood that the electrode arrangement shown there, as shown in the FIGS. 6, 7 and 8, is cast into the peripheral wall 34 of the endoscope head 8. If the electrodes 46', 48' are cast into the peripheral wall 34, electroactive polymer material is located between the electrodes 46' and 48', and this forms a dielectric and changes its extension in the axial direction X under a voltage applied between the electrodes 46' and 48'.

Force sensors 58 are arranged in the endoscope tip 10 at several peripheral positions as shown in FIG. 7. The force sensors 58 are in each case formed of two electrodes 60 and 62 which are embedded into the polymer material of the walls 34 and 36 and are distanced to one another. The electrodes 60 and 62 are connected to control leads 50 in the axial direction, which extend to the proximal end of the instrument and there are connected to the control device 32 via the connection cable 12. The force sensors 58 operate in a manner such that on deformation of the polymer material between the electrodes 60 and 62, this material changes its capacitance and/or electrical resistance, which may be detected by the electrodes 60 and 62. For this, the electrodes 60 and 62 are connected to the control device 32 via control leads 50, and the control device detects the resistance or the capacitance between the electrodes 60 and 62. Then, in dependence on the detected capacitance or the electrical resistance, one may deduce the acting force given the knowledge of the modulus of elasticity of the polymer of the wall 34 and 36. Forces with components from the axial direction and radial direction may be detected by the force sensors 58 due to the fact that the electrodes 60 and 62 are arranged inclined to the longitudinal axis X and the end-face of the endoscope tip 10, here at an angle of essentially 45°. Moreover, several force sensors 58 are arranged distributed over the periphery of the endoscope tip 10. Thus, with a selective evaluation of the signals of the individual force sensors 58, the control device 32 may recognize, in which peripheral region a force is exerted onto the endoscope tip 10. Such a force in particular is produced by an advance when the endoscope tip 10 comes up against an obstacle.

If now the obstacle is located in only one peripheral region, the endoscope may circumnavigate this obstacle by the deflection of the endoscope head 8, firstly of the region 20 (see FIG. 2). The control device 32 for this is designed such that it permits an automatic deflection, when the endoscope tip 10 meets an obstacle. Then, the control device 32 ascertains in which peripheral region the obstacle lies, depending on which of the force sensors 58 signals an increased force. Subsequently, the electrodes 46 and 48 are subjected to voltage in those actuator fields 52, which cause a deflection of the endoscope head 8 in a radial direction which is distant or opposite to the detected force. In this manner, the endoscope tip 10 is deflected or bent away from the obstacle in the radial direction, so that the endoscope tip 10 and, with a further advance, the endoscope head 8, may be led around the obstacle.

Thereby, usefully a continuous force monitoring at the force sensors 58, and an immediate control of the associated actuators or electrodes 46 and 48 by the control device 32 is effected, so that as a whole, the serpentine movement of the endoscope head 8 described with regard to FIG. 2 may be achieved.

If several or all force sensors 58 signal an increased force, then this may be deduced as a force acting frontally in the axial direction X. This means a frontal collision with an obstacle. In such a case, the control device 32 may not recognize without further ado, as to the direction in which the endoscope head 8 must be deflected, in order to pass the obstacle. In this case, an alarm signal may be emitted from the control device 32 via an alarm device 64, which signals the obstacle to the operating person. The alarm device 64 may be designed as an optical display, as an acoustic display, as an acoustic indicator or as haptic indicator. The haptic indicator may, for example, be a vibration in the hand grip or something similar. Moreover, it is also possible for the control device 32 to automatically control the advance. In such a case, the advance may be stopped given a frontal collision.

In order to produce the serpentine movement which was described by FIG. 2, the control device 32 must further obtain information on the travelled advance path. For this, a detection device 66 for detecting the travelled advance path may be provided. This may, for example, be arranged in a fixed point, compared to which the relative axial movement of the shank 4 is detected. The electrical resistance of the polymer changes depending on the extension or compression of the polymer between the electrodes 46, 46' and 48, 48', which may be detected via the electrodes 46, 46' and 48, 48'.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An endoscopic instrument comprising a shank (4), which is bendable in at least one section, an endoscope head (8), which forms the distal end of the shank (4) and in which distal-side interfaces of the instrument are arranged, wherein the endoscope head (8) is bendable, and wherein the endoscope head (8) includes a peripheral side wall (34) and a distal end wall (36) designed as one piece from an electro-active polymer, and electrodes (46, 48) arranged in the endoscope head (8) in the polymer, which electrodes may be subjected to electrical voltage.

2. The endoscopic instrument according to claim 1, wherein the electrodes (46, 48) are cast into the polymer.

3. The endoscopic instrument according to claim 1, wherein the electrodes (46, 48) comprise at least one electrode group comprising at least one control electrode (46) and at least one reference electrode (48).

4. The endoscopic instrument according to claim 3, wherein the endoscope head (8) comprises several electrode groups (52), which are arranged at different angular positions with respect to a longitudinal axis X of the instrument.

5. The endoscopic instrument according to claim 3, wherein the endoscope head (8) comprises several electrode groups (52), which are arranged at different axial positions with regard to a longitudinal axis X of the instrument.

6. The endoscopic instrument according to claim 3, wherein at least one electrode group (52) is provided, which comprises several control electrodes (46) spaced from one another in an axial direction X with respect to a longitudinal axis of the instrument, and which may be subjected to voltage.

7. The endoscopic instrument according to claim 6, wherein the several control electrodes (46) are subjected to voltage independently of one another.

8. The endoscopic instrument according to claim 6, wherein the electrode group (52) comprises a multitude of control electrodes (46) and a multitude of reference electrodes (48), which are arranged alternating with one another in the axial direction X.

9. The endoscopic instrument according to claim 8, wherein the multitude of control electrodes (46) and the multitude of reference electrodes (48) are designed in each case as a comb structure, and the two comb structures mesh into one another with their teeth.

10. The endoscopic instrument according to claim 6, wherein the reference electrodes (48') are designed in a helical manner and the control electrodes (46') are arranged between individual helix flights of the reference electrode (48').

11. The endoscopic instrument according to claim 3, wherein a plurality of electrode groups (52) have a common reference electrode (48).

12. The endoscopic instrument according to claim 11, wherein the common reference electrode (48) has a helical form.

13. The endoscopic instrument according to claim 1, wherein the shank (4) on a proximal side of the endoscope head (8) comprises at least one further bendable section of an electro-active polymer with electrodes arranged therein.

14. The endoscopic instrument according to claim 1, wherein the electrodes (46, 48) are connected to control leads (50), which extend to a proximal end of the shank (4).

15. The endoscopic instrument according to claim 1, wherein the endoscope head (8) comprises at least one force sensor (58) arranged at a distal end.

16. The endoscopic instrument according to claim 15, wherein the force sensor (58) is embedded into the electro-active polymer.

17. The endoscopic instrument according to claim 1, further comprising an electronic control device (32), which is connected to the electrodes (46, 48) and controls deformation of the shank (4).

* * * * *